United States Patent [19]

Meier et al.

[11] Patent Number: 5,455,369

[45] Date of Patent: Oct. 3, 1995

[54] PROCESS FOR THE MANUFACTURE OF METHYL CYANOACRYLATE

[75] Inventors: Eric A. Meier, N. Brunswick; Dilip K. Ray-Chaudhuri; Jules E. Schoenberg, both of Bridgewater, all of N.J.

[73] Assignee: National Starch and Chemical Investment Holding Corporation, Wilmington, Del.

[21] Appl. No.: 348,524

[22] Filed: Dec. 2, 1994

[51] Int. Cl.⁶ ................................................. C07C 253/30
[52] U.S. Cl. ................................................. 558/372
[58] Field of Search ...................................... 558/372

[56] References Cited

U.S. PATENT DOCUMENTS

| 2,467,927 | 4/1949 | Ardis | 260/465.4 |
|---|---|---|---|
| 2,721,858 | 10/1955 | Joyner et al. | 260/67 |
| 2,756,251 | 7/1956 | Joyner et al. | 260/465.4 |
| 2,912,454 | 11/1959 | McKeever | 260/465.4 |
| 2,926,188 | 2/1960 | McKeever et al. | 260/465.4 |
| 3,254,111 | 5/1966 | Hawkins et al. | 260/465.4 |
| 3,444,233 | 5/1969 | Rabinowitz | 558/372 |
| 3,465,027 | 9/1969 | Hawkins | 260/464 |
| 4,421,909 | 12/1983 | Gruber et al. | 528/362 |
| 4,764,545 | 8/1988 | Yosida | 523/212 |

*Primary Examiner*—Joseph Paul Brust
*Attorney, Agent, or Firm*—Jane E. Gennaro

[57] ABSTRACT

A process for preparing methyl α-cyanoacrylate in which methyl cyanoacetate is reacted with formaldehyde to form a polymer, which is subsequently depolymerized to the monomeric product, comprises using an ester of poly(ethylene glycol) as the solvent for the polymerization and depolymerization reactions.

2 Claims, No Drawings

PROCESS FOR THE MANUFACTURE OF METHYL CYANOACRYLATE

FIELD OF THE INVENTION

This invention relates to a process for preparing high purity methyl cyanoacrylate in good yield. More specifically, it relates to the use of a class of solvents, bis-alkanoate esters of polyethyleneglycol, to achieve the high purity and good yield.

BACKGROUND OF THE INVENTION

α-Cyanoacrylates, important compounds in the manufacture of adhesive compositions, are produced industrially by reacting a cyanoacetate with formaldehyde or a polymer of formaldehyde to obtain a crude polymeric condensation product. This crude polymeric product is then depolymerized with heat and acid to yield the monomeric α-cyanoacrylate. One of the more important cyanoacrylates is methyl a-cyanoacrylate.

The basic chemical reactions for the formation of the methyl α-cyanoacrylate can be represented by the equations:

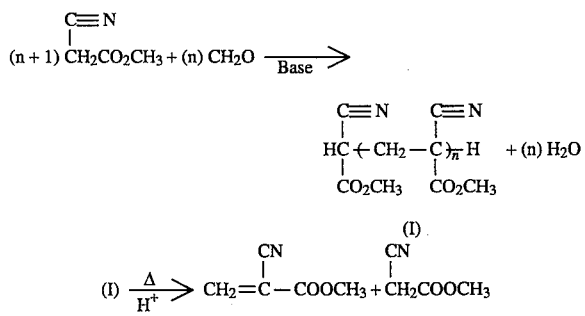

The depolymerization yields the desired methyl cyanoacrylate, and methyl cyanoacetate. It is difficult to separate methyl cyanoacrylate from methyl cyanoacetate by distillation because the boiling points fall close together. These equations show that more methyl cyanoacrylate can be obtained relative to methyl cyanoacetate the higher the molecular weight of the polymer (I). Nevertheless, in the past, the production of high molecular weight polymers has been avoided.

In the usual prior art process, the initial condensation reaction between the cyanoacetate and formaldehyde is conducted in a low molecular weight volatile organic solvent that is essentially insoluble in water, such as butyl acetate, benzene, toluene, heptane, or cyclohexane. These organic solvents have been the preferred reaction medium because they act as azeotroping solvents (with the water resulting from the condensation reaction) permitting the water to be removed along with the solvent by distillation.

The problem with this process is that high molecular weight polymers, which result in a higher percentage of purity for the final product, precipitate out of these solvents. In addition, these solvents frequently contaminate the final product, are extremely volatile and flammable, thus creating environmental and safety problems in practice.

Purer α-cyanoacrylate products can be obtained, and safety and environmental problems be reduced, if the azeotroping solvent can be eliminated from the manufacturing process.

SUMMARY OF THE INVENTION

This invention is an improvement in the process for manufacturing α-cyanoacrylates that comprises using esters of poly(ethylene glycol) (PEG), in particular PEG diacetate, propionate and butyrate, as the solvent for both the initial condensation reaction between the cyanoacetate and formaldehyde and the subsequent depolymerization reaction to obtain the α-cyanoacrylate.

DETAILED DESCRIPTION OF THE INVENTION

The instant process is conducted in an ester of poly(ethylene glycol) (PEG), preferably PEG diacetate, which is easily prepared by known syntheses. The PEG will have a number average molecular weight of 200–1000. PEG diacetate is an excellent solvent for both the polymer (I) and for the methyl cyanoacrylate. While the polymer (I) is being made, water formed during the reaction is removed under vacuum. No azeotroping solvent is required, although a small amount can be added to facilitate removal of water.

In the usual prior art process, the crude polymeric residue is pyrolyzed under vacuum with acid and heat after the azeotroping solvent is distilled off, and the monomeric vapor evolved from the polymer is condensed and recovered. In the inventive process, because the PEG diacetate has a vapor pressure lower than the vapor pressure of methyl cyanoacrylate, the cyanoacrylate product can be distilled off during the depolymerization process, leaving the solvent behind. This reduces or eliminates contamination from the solvent in the final product. Purity of yields obtained by prior methods was typically 90–95% Purity of yields from this process is 96% or better.

The reaction between the cyanoacetate and the formaldehyde to form the polymeric α-cyanoacrylate is readily effected by heating the reaction mixture to a temperature of about 50° to 90° C. in the presence of a basic catalyst or a salt of a weak acid or weak base. Many basic condensation catalysts are known, and any of those can be used to catalyze the reaction. Preferred catalysts are piperidine, pyrrolidine or sodium hydroxide, used in an amount of about 0.1 to 0.5 percent by weight.

The depolymerization reaction is conducted by heating the polymer at low pressure and in the presence of both anionic and free-radical polymerization inhibitors. The anionic polymerization inhibitors are typically both volatile and nonvolatile acidic substances. Suitable nonvolatile inhibitors include polyphosphoric acid, toluenesulfonic acid, sulfuric acid, phosphorous. pentoxide, antimony pentoxide, picric acid, metaphosphoric acid, maleic anhydride, ferric chloride, and the like. Suitable volatile acidic inhibitors include sulfur dioxide, nitric oxide, hydrogen chloride, hydrogen fluoride, and the like. Usually, it is preferable to include a nonvolatile inhibitor in both the depolymerization reaction vessel and in the receiving vessel collecting the depolymerization vapors. The nonvolatile inhibitor is removed by redistilling the methyl cyanoacrylate. During depolymerization and redistillation it is also preferable to introduce a stream of volatile inhibitor into the system, which then mixes with the monomeric product vapors evolved and, to some extent, dissolves in the monomeric product when the vapor is condensed. Phosphorous pentoxide, polyphosphoric acid, and toluenesulfonic acid are the preferred nonvolatile inhibitors for the depolymerization stage, and sulfur dioxide is the preferred volatile inhibitor. Free radical inhibitors are also added to the depolymerization reaction. Suitable inhibitors are hydroquinone, catechol, pyrogallol and methyl ether of hydroquinone.

EXAMPLES

The synthesis is carried out in three steps: 1) reaction of methyl cyanoacetate with formaldehyde to produce poly(methyl cyanoacrylate) and water; 2) depolymerization of poly(methyl cyanoacrylate) under acidic conditions to produce crude methyl cyanoacrylate; 3) redistillation of the crude methyl cyanoacrylate. Products were analyzed by proton NMR in chloroform-d using a Bruker AM 300 NMR spectrometer. The following components were present in the products:

| Compound | Protons used in Quanitation | Chemical Shift (ppm) |
| --- | --- | --- |
| methyl-2-cyanoacrylate | $CH_2=C-CO_2\underline{CH_3}$ with $C\equiv N$ | 3.85 |
| methyl cyanoacetate | $NC-\underline{CH_2}CO_2CH_3$ | 3.47 |
| methyl-2-cyanopropionate | $CH_3-\underline{CH}CO_2CH_3$ with $C\equiv N$ | 1.59 |
| trimethyl phosphate | $(\underline{CH_3}O)_3PO$ | 3.77 |

Example 1

Use of PEG 200 diacetate as a solvent and cyclohexane as an azeotrope agent.

The following ingredients were combined in a one liter flask fitted with stirrer, thermometer and a Dean-Stark receiver filled with cyclohexane: 63.2 g (2.0 moles) of 95% paraformaldehyde (active formaldehyde=95%) (reactant); 208.0 g (2.10 moles) of methyl cyanoacetate (reactant); 25 ml of cyclohexane (to provide reflux for water removal); 275 ml of PEG 200 diacetate; 1.0 g of piperidinium acetate (catalyst). The mixture was refluxed until all the water of reaction was removed (4 hours). The solution was cooled, treated with 3.1 g of p-toluenesulfonic acid monohydrate and 3.0 g of polyphosphoric acid, and refluxed for ½ hour. Hydroquinone (1.0 g) was then added. The flask was immersed in a hot oil bath and the cyclohexane was distilled out. Vacuum was then applied and the product was distilled in a stream of sulfur dioxide at a vacuum of 2 to 4 mm Hg at a vapor temperature of 84° to 124° C. The product, 181.8 g, was collected in a flask containing a small amount of hydroquinone and polyphosphoric acid. The product was redistilled at 4 mm Hg and at 58°–64° C. The yield was 103.1 g.

The product contained the following ingredients:

| methyl-2-cyanoacrylate | 97 mole % |
| --- | --- |
| methyl cyanoacetate | 1 mole % |
| trimethyl phosphate | 0.4 mole % |

Example 2

Use of PEG 400 diacetate as a solvent and cyclohexane as an azeotrope agent.

The previous example was repeated except that PEG 400 diacetate was used in place of PEG 200 diacetate. The polymer precipitated from solution after about one hour at reflux, which indicated that a mixture of PEG 400 diacetate and cyclohexane is not a suitable solvent for poly(methyl cyanoacrylate). The experiment was discontinued.

Example 3

Use of PEG 400 diacetate as a solvent without an azeotroping solvent.

In this example, the cyclohexane, which proved to be a poor solvent for poly(methyl cyanoacrylate), was not added and the depolymerization was run under vacuum to assist removal of water.

PEG 400 diacetate (596 g) and 2.0 g of piperidinium acetate were combined in a two liter flask fitted with a stirrer, thermometer, and condenser set for vacuum distillation. The mixture was heated to 60° C and treated over a one hour period with a slurry of 126.4 g (4.0 moles) of 95% paraformaldehyde in 416.0 g (4.2 moles) of methyl cyanoacetate. The mixture was heated in an oil bath set at 120° C. while vacuum was gradually applied, ending at a final pressure of 1 mm Hg. After water ceased to evolve, the reaction mixture was treated with 6.2 g of p-toluenesulfonic acid monohydrate, 6.0 g of polyphosphoric acid, and 2.0 g of hydroquinone and heated at 120° C. for one hour. The depolymerization was then carried out in the same manner as in Example 1. The yield was 322.0 g; the redistilled yield was 265.5 g.

The product contained the following components:

| methyl-2-cyanoacrylate | 98 mole % |
| --- | --- |
| methyl cyanoacetate | 1 mole % |
| methyl-2-cyanopropionate | 1 mole % |

Example 4

Use of azeotroping solvent.

The following ingredients were combined in a one liter flask fitted with stirrer, thermometer and a Dean-Stark receiver filled with cyclohexane: 31.6 g (1.0 mole) of 95% paraformaldehyde (active formaldehyde=95%) (reactant); 104.0 g (1.05 moles) of methyl cyanoacetate (reactant); 130 ml of butyl acetate (as azeotroping solvent for water removal); 1.0 g of piperidinium acetate (catalyst). The mixture was refluxed for 30 minutes, at which time the crude polymer precipitated out of solution, and the mixture became unstirrable. The reaction was discontinued.

We claim:

1. In a process for preparing methyl α-cyanoacrylate, in which methyl cyanoacetate is reacted with formaldehyde to form a polymer that is then depolymerized to the monomeric product, and in which the purity of yield is 96% or better, the improvement comprising conducting the process in a poly(ethylene glycol) diacetate, dipropionate, or dibutyrate, having a number average molecular weight of 200–400 as the solvent.

2. The improvement according to claim 1 in which the poly(ethylene glycol) diacetate, dipropionate, or dibutyrate, has a number average molecular weight of 200–1000 and is the sole solvent for the process.

* * * * *